United States Patent
Jandhyala et al.

(10) Patent No.: US 11,531,006 B2
(45) Date of Patent: Dec. 20, 2022

(54) METHODS AND SYSTEMS FOR CHARACTERIZING MULTIPLE PROPERTIES OF CEMENT USING P-WAVES OF MULTIPLE FREQUENCIES

(71) Applicant: Halliburton Energy Services, Inc., Houston, TX (US)

(72) Inventors: Siva Rama Krishna Jandhyala, Maharashtra (IN); Walmy Cuello Jiminez, Houston, TX (US); Ganesh Shriniwas Pangu, Maharashtra (IN); Abhimanyu Pramod Deshpande, Maharashtra (IN); Ketan Chimanlal Bhaidasna, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 564 days.

(21) Appl. No.: 16/635,103

(22) PCT Filed: Sep. 18, 2017

(86) PCT No.: PCT/US2017/052018
§ 371 (c)(1),
(2) Date: Jan. 29, 2020

(87) PCT Pub. No.: WO2019/055043
PCT Pub. Date: Mar. 21, 2019

(65) Prior Publication Data
US 2020/0249204 A1 Aug. 6, 2020

(51) Int. Cl.
*G01N 29/07* (2006.01)
*E21B 47/003* (2012.01)
(Continued)

(52) U.S. Cl.
CPC ............ *G01N 29/07* (2013.01); *E21B 47/003* (2020.05); *E21B 47/06* (2013.01); *G01N 29/024* (2013.01);
(Continued)

(58) Field of Classification Search
CPC ...... G01N 29/07; G01N 29/024; G01N 29/46; G01N 29/032; G01N 29/11; G01N 29/348;
(Continued)

(56) References Cited

U.S. PATENT DOCUMENTS

| 5,121,629 A | 6/1992 | Alba |
| 5,412,990 A * | 5/1995 | D'Angelo ................ G01H 5/00 374/53 |

(Continued)

OTHER PUBLICATIONS

International Search Report and Written Opinion issued in related PCT Application No. PCT/US2017/052018 dated Jan. 2, 2018, 21 pages.

(Continued)

*Primary Examiner* — Suman K Nath
(74) *Attorney, Agent, or Firm* — Thomas Rooney; C. Tumey Law Group PLLC

(57) ABSTRACT

Methods and systems for characterizing multiple properties of a cement composition for use at downhole conditions using ultrasonic analysis tools are provided. In some embodiments, the methods comprise: transmitting at least a first p-wave and a second p-wave having different frequencies through a cement composition; determining velocities of the first and second p-waves through the sample; transmitting at least a third p-wave having a third frequency through the cement composition while allowing the cement composition to at least partially hydrate, wherein the third frequency is higher than the second frequency; determining at least a velocity of the third p-wave through the cement (Continued)

composition; based at least in part on the velocities of the p-waves, determining at least the compressibility, Poisson's ratio, Young's modulus, and shear modulus of the cement composition.

13 Claims, 7 Drawing Sheets

(51) Int. Cl.

| | | |
|---|---|---|
| *E21B 47/06* | (2012.01) | |
| *G01N 29/024* | (2006.01) | |
| *G01N 29/032* | (2006.01) | |
| *G01N 29/11* | (2006.01) | |
| *G01N 33/38* | (2006.01) | |

(52) U.S. Cl.
CPC ........... *G01N 29/032* (2013.01); *G01N 29/11* (2013.01); *G01N 33/383* (2013.01); *G01N 2291/011* (2013.01); *G01N 2291/015* (2013.01); *G01N 2291/0232* (2013.01); *G01N 2291/02827* (2013.01)

(58) Field of Classification Search
CPC ....... G01N 2291/011; G01N 2291/015; G01N 2291/0232; G01N 2291/02827; G01N 2291/02416; G01N 2291/0251; G01N 2291/02809; G01N 2291/0421; G01N 2291/102; G01N 33/383; E21B 47/003; E21B 47/06

See application file for complete search history.

(56) References Cited

U.S. PATENT DOCUMENTS

| | | |
|---|---|---|
| 5,992,223 A | 11/1999 | Sabins et al. |
| 2008/0148852 A1 | 6/2008 | Maki et al. |
| 2009/0205427 A1 | 8/2009 | Lootens et al. |
| 2011/0083503 A1 | 4/2011 | Iverson et al. |
| 2016/0040531 A1* | 2/2016 | Ramakrishnan ......... G01V 3/38 702/11 |
| 2016/0047238 A1 | 2/2016 | Zeroug et al. |
| 2016/0109593 A1* | 4/2016 | Saxena ................... G06F 17/16 703/2 |
| 2019/0317071 A1* | 10/2019 | Bois ..................... G01N 33/383 |

OTHER PUBLICATIONS

Castagna, John P., Michael L. Batzle, and Raymond L. Eastwood. "Relationships between compressional-wave and shear-wave velocities in clastic silicate rocks." geophysics 50.4 (1985): 571-581.

Matsukawa, Mami, and Isao Nagai. "Ultrasonic characterization of a polymerizing epoxy resin with imbalanced stoichiometry." The Journal of the Acoustical Society of America 99.4 (1996): 2110-2115.

Bouzidi, Youcef, and Douglas R. Schmitt. "Measurement of the speed and attenuation of the Biot slow wave using a large ultrasonic transmitter." Journal of Geophysical Research: Solid Earth 114.B8 (2009).

Johnson, David Linton, and Thomas J. Plona. "Acoustic slow waves and the consolidation transition." The Journal of the Acoustical Society of America 72.2 (1982): 556-565.

Sayers, C. M., and R. L. Grenfell. "Ultrasonic propagation through hydrating cements." Ultrasonics 31.3 (1993): 147-153.

Moon, Jeff, and Steven Wang. "Acoustic method for determining the static gel strength of slurries." SPE Rocky Mountain Regional Meeting. Society of Petroleum Engineers, 1999.

Trtnik, Gregor, Franci Kavčič, and Goran Turk. "Prediction of concrete strength using ultrasonic pulse velocity and artificial neural networks." Ultrasonics 49.1 (2009): 53-60.

Zhu, Jinying, et al. "Effects of air voids on ultrasonic wave propagation in early age cement pastes." Cement and Concrete Research 41.8 (2011): 872-881.

* cited by examiner

METHODS AND SYSTEMS FOR CHARACTERIZING MULTIPLE PROPERTIES OF CEMENT USING P-WAVES OF MULTIPLE FREQUENCIES

CROSS-REFERENCE TO RELATED APPLICATION

The present application is a U.S. National Stage Application of International Application No. PCT/US2017/052018 filed Sep. 18, 2017, which is incorporated herein by reference in its entirety for all purposes.

The present disclosure relates generally to well cementing and completion operations, and more particularly, to characterizing certain properties of a cement composition for use at downhole conditions.

Well cementing and completion operations typically require the use of casings within a wellbore in a subterranean formation to ensure that the wellbore does not collapse once it is drilled and that sensitive areas of the formation are protected and isolated. In most instances, the casings are secured in the wellbore using a cement layer that fills an annulus between and bonds to both the casing and the formation. Cements also may be placed in other regions of a subterranean formation, among other reasons, for various remedial applications to strengthen those regions of a formation and prevent their collapse, and/or to isolate a particular region of a formation from other regions therein. The strength and/or other properties of the cement may be tailored to the conditions in the formation, the intended function of the cement, and/or other factors.

Some cement evaluation tools such as ultrasonic cement analyzers (UCA) emit a high frequency ultrasonic pulse into one end of the sample of the cement and receive a signal on the other end of the sample of corresponding to the emitted pulse after it has traveled through the cement sample. The speed at which the ultrasonic pulse travels through the cement sample may be correlated to the compressive strength of the cement, and thus the compressive strength of the cement may be estimated or calculated based on the change in velocity of the ultrasonic pulse transmitted through the cement sample as it cures. Ultrasonic cement analyzers thus may provide a nondestructive method for calculating or estimating the compressive strength of a cement as it cures at simulated well bore conditions.

BRIEF DESCRIPTION OF THE DRAWINGS

Some specific exemplary embodiments of the disclosure may be understood by referring, in part, to the following description and the accompanying drawings.

Figure 1A:
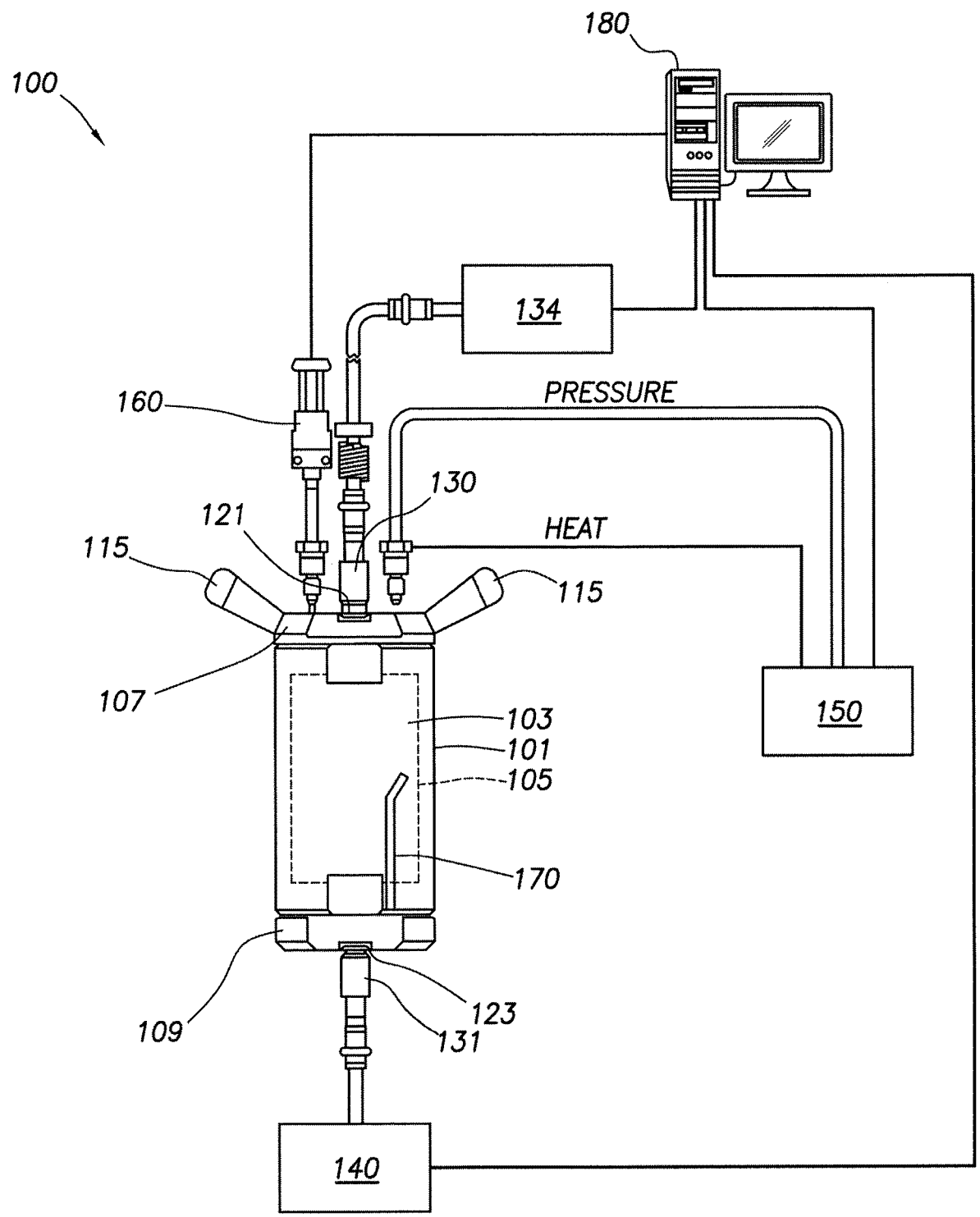
FIG. 1A is a diagram illustrating an example of an ultrasonic analysis system that may be used in accordance with certain embodiments of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to well cementing and completion operations, and more particularly, to characterizing multiple properties of a cement composition for use at downhole conditions using ultrasonic analysis tools.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. It may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation specific decisions are made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented using a tool that is made suitable for testing, retrieval and sampling along sections of the formation. Embodiments may be implemented with tools that, for example, may be conveyed through a flow passage in tubular string or using a wireline, slickline, coiled tubing, downhole robot/tractor or the like.

The terms "couple" or "couples" as used herein are intended to mean either an indirect or a direct connection. Thus, if a first device couples to a second device, that connection may be through a direct connection or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

The present disclosure provides methods and systems for characterizing multiple properties of a hydratable cement composition over a period of time as the cement composition hydrates, including at least the Young's modulus, Poisson's ratio, shear modulus, and compressibility (inverse of bulk modulus) of the cement composition, using an ultrasonic analysis tool. Optionally, one or more other properties of the cement composition may be characterized in certain embodiments of the present disclosure, including but not limited to static gel strength, change in hydration volume, and/or compressive strength of the cement composition. The properties of the cement composition such as those listed above and discussed elsewhere herein may be calculated or otherwise characterized as sonic versions of these properties, which may be converted to their static and/or mechanical equivalents using correlation constants and/or other mathematical correlations. For purposes of this disclosure, references to any of these properties may include either the sonic property or any static or mechanical equivalent thereof obtained with such correlations.

In the methods and systems of the present disclosure, the properties referenced above may be characterized using an ultrasonic analysis system that emits and detects sonic signals comprised of p-waves (also known as compression waves) at multiple different frequencies. In particular, the ultrasonic analysis system may be configured to emit and detect at least a first p-wave or set of p-waves having a relatively high frequency and a second p-wave or set of p-waves having a relatively low frequency that are transmitted through the cement composition sample, and monitor the velocity of those p-waves over a period of time during the hydration process. These p-waves of different frequencies may be transmitted through the cement composition sample and/or monitored substantially continuously over a period of time in order to assess the properties of the cement composition throughout the hydration process. These p-waves of different frequencies may travel through the cement composition and/or interact with the different phases thereof differently at different points in time during the hydration process. For example, the solid and liquid phases of the cement composition may vibrate in phase with each other when a p-wave having a relatively higher frequency travels through the sample, while the solid and liquid phases of the cement composition may vibrate out of phase with each other when a p-wave having a relatively low frequency travels through the sample. Thus, the use of p-waves of different frequencies may facilitate determination of properties of the cement composition other than its compressive strength, and also may facilitate the more accurate determination of properties in the cement composition at various points in time as the cement hydrates. In some embodiments, the ultrasonic analysis system further may be configured to detect the amplitude of those p-waves, among other reasons, to provide data for calculating certain properties and/or to detect other phenomena in the cement composition during the test.

Among the many potential advantages to the methods and systems of the present disclosure, only some of which are alluded to herein, the methods and systems of the present disclosure may provide techniques for measuring multiple mechanical properties of a cement composition sample using a single method or system. This may, among other benefits, reduce the amount of time, the number of iterative tests, and/or the different types of testing apparatus needed to obtain information regarding various properties of a cement composition at downhole conditions. By providing techniques for determining multiple properties using a single system, the methods and systems of the present disclosure may reduce the physical space or footprint needed to accommodate testing equipment, either at a well site or in a laboratory. In some embodiments, these methods and systems may provide non-destructive techniques for determining one or more of the aforementioned properties and/or techniques that may be used at a well site where subterranean cementing operations are to be conducted. In some embodiments, the methods and systems of the present disclosure may provide more accurate data regarding the compressibility and/or other properties of the cement composition early in the hydration process (e.g., before the cement reaches its percolation threshold) as compared to conventional techniques for determining those properties. One or more of these benefits may facilitate the selection of cement compositions for subterranean cementing operations that are better suited to the particular conditions of the operation.

The p-waves employed in the methods and systems of the present disclosure may have any frequencies that can be detected and distinguished from one another after the waves have traveled through the cement composition sample, with a first p-wave having a higher frequency than a second p-wave. In some embodiments, the frequency of the first p-wave may range from about 400 kHz to about 1000 kHz, or from about 600 kHz to about 800 kHz. In some embodiments, the frequency of the second p-wave may range from about 30 kHz to about 400 kHz, or from about 50 kHz to about 200 kHz.

At various stages during the hydration process, cement compositions may behave as different types of substances, and thus their mechanical properties may be measured in differently depending upon the stage of hydration. In some embodiments, cement compositions may behave as a suspension before they reach their percolation threshold, then as a fluid saturated porous media for a period of time after they reach their percolation threshold, and finally as a solid after considerable hydration has occurred and strength is attained. In some embodiments, the "percolation threshold" of a cement composition may be the point in time during the hydration process when the solids in the cement composition have sufficient grain-to-grain contact, or the matrix of the cement composition is otherwise sufficiently established, to pass a wave from one end of the cement composition sample to the other end of the sample through the solid matrix only without having to pass the wave through the liquid in which the matrix is embedded. However, it is recognized that other definitions or concepts may be used to define a percolation threshold for a particular cement composition, and those definitions or concepts also may be applied in the methods and systems of the present disclosure. As discussed below, different formulas and data may be used to calculate properties of the cement composition before and after the cement composition sample reaches its percolation threshold. For example, data relating to the p-waves having a relatively lower frequency may not be needed to calculated, and thus in some embodiments, those p-waves may or may not be monitored once the cement composition sample reaches its percolation threshold.

In some embodiments, the ultrasonic analysis tool and/or equipment coupled thereto may be used to determine when the cement composition sample being analyzed has reached its percolation threshold using any suitable means. For example, the attenuation of waves that travel through the sample may be lessened once the sample reaches its percolation threshold, and thus the ultrasonic analysis system of the present disclosure may be able to ascertain when the percolation threshold has been reached based on a detected increase in the amplitude in waves that have traveled through the cement composition sample. In other embodiments, the percolation threshold of the cement composition may be determined or estimated using literature values or otherwise previously-observed values and thus applied in determining the properties of the cement composition sample.

In some embodiments, the ultrasonic analysis tool may comprise a conventional and/or commercially-available ultrasonic cement analyzer (UCA) system that has been modified to emit and monitor both p-waves of different frequencies, which may be accomplished by changing the transmitter and receiver frequency of the UCA system. Such commercially-available UCA systems may include, but are not limited to, UCA systems available from Fann Instrument Company and/or Chandler Engineering LLC (a division of AMETEK, Inc.). As a person of skill in the art with the benefit of this disclosure will recognize, the hardware and/or software of existing computerized UCA systems (e.g., UCA systems that are operated using a computer processor or other information handling system) also may require certain alterations to accommodate data relating to the p-waves of different frequencies.

FIG. 1A is a diagram illustrating an example of an ultrasonic analysis system that may be used in accordance with certain embodiments of the present disclosure. Referring now to FIG. 1A, the system 100 includes a pressure vessel 101 comprising an internal cell 103 in which a sample of the cement composition (e.g., a cement slurry) is placed. The cell 103 is defined by cell housing or cylinder wall or vessel wall 105, upper end cap 107 and by lower end cap 109. Pressure vessel 101 may be lifted using handles 115. Seals (not shown) that may be constructed of elastomer and metal form a seal between wall 105 and end caps 107 and 109. Upper physical contact 121 is located on an upper surface of upper end cap 107, and lower physical contact 123 is located on a lower end of lower end cap 109. In the embodiment shown, the upper surface of a plug at physical contact 121 is coupled to a transducer (acoustic receiver) 130 which is then coupled to an electrical receiver 134. The lower surface of a plug at physical contact 123 is coupled to another transducer (acoustic transmitter) 131 which is then coupled to an electrical transmitter 140. In some embodiments, the interfaces between the surfaces of transducers 130 and 131 (e.g., metal, ceramic, plastic, etc.) and the end caps 107 and 109 (e.g., metal or ceramic) should comprise a physical contact with minimal air gap or moisture between their surfaces. In some embodiments, this may be accomplished by providing ultrasonic conductive gels or other like substances on those surfaces at the points of contact. As a person of ordinary skill in the art will recognize with the benefit of this disclosure, these connections of the transducer/receiver and the transmitter at the upper and lower ends of the pressure vessel 101 may be reversed in other embodiments of the present disclosure. Unlike conventional UCA systems, transmitter 140, transducers 130 and 131, and receiver 134 are configured to emit and/or detect waves or signals of a desired amplitude at at least two different frequencies, i.e., the relatively higher and lower frequencies of the p-waves discussed herein. In some embodiments, the receiver further may be configured to measure the amplitude or intensity of waves or signals that it receives. In other embodiments the system may be designed to sweep a frequency range and gather information on frequency, amplitude and time of travel in a substantially continuous manner.

The pressure vessel 101 is further coupled to a pressure and heat source 150 such as an autoclave, which may be used to create the temperature and pressure conditions that the cement composition would experience when placed in a subterranean formation or well bore in the pressure vessel 101. In other embodiments, various pumps or vacuum systems may be used to change the pressure conditions within the pressure vessel 101, and various types of cooling or heating mechanisms may be used to change the temperature conditions inside the pressure vessel 101. The pressure vessel 101 also may be coupled to a thermocouple 160, which may be used to monitor the temperature therein.

In the embodiment shown, the pressure vessel 101 may be fitted with one or more mixing devices 170 that are disposed in or extend into cell 103 that may be used to mix the cement slurry within the cell 103 before measurements are taken. The mixing device 170 may comprise any device suited for mixing (e.g., stirring, agitating, circulating, or plunging device) a hydratable cement composition, which often comprises a mixture, slurry, or suspension of cementitious solid materials in water or another aqueous fluid. Mixing devices that may be suitable in certain embodiments of the present disclosure include, but are not limited to, magnetic stir bars, stirring rods or arms, plungers, floating ring pistons, blending devices, and the like. The mixing device 170 may be activated or used once the cement composition sample is placed in the cell 103 for some period of time (e.g., several minutes to several hours) before any wave transmission through the cement sample is monitored. This may, among other benefits, reduce or eliminate prior conditioning of the cement composition sample that must be performed before it is placed in the cell 103 for analysis. It is recognized that, in some instances, the presence and/or use of a mixing device such as the one shown may interfere with the transmission of waves through the cement sample, and thus may not be desirable for use in those embodiments. In some embodiments, the mixing device 170 may be deactivated and/or removed from the internal cell 103 before measurements are taken so that the mixing device does not interfere with wave transmission.

Figure 1B:
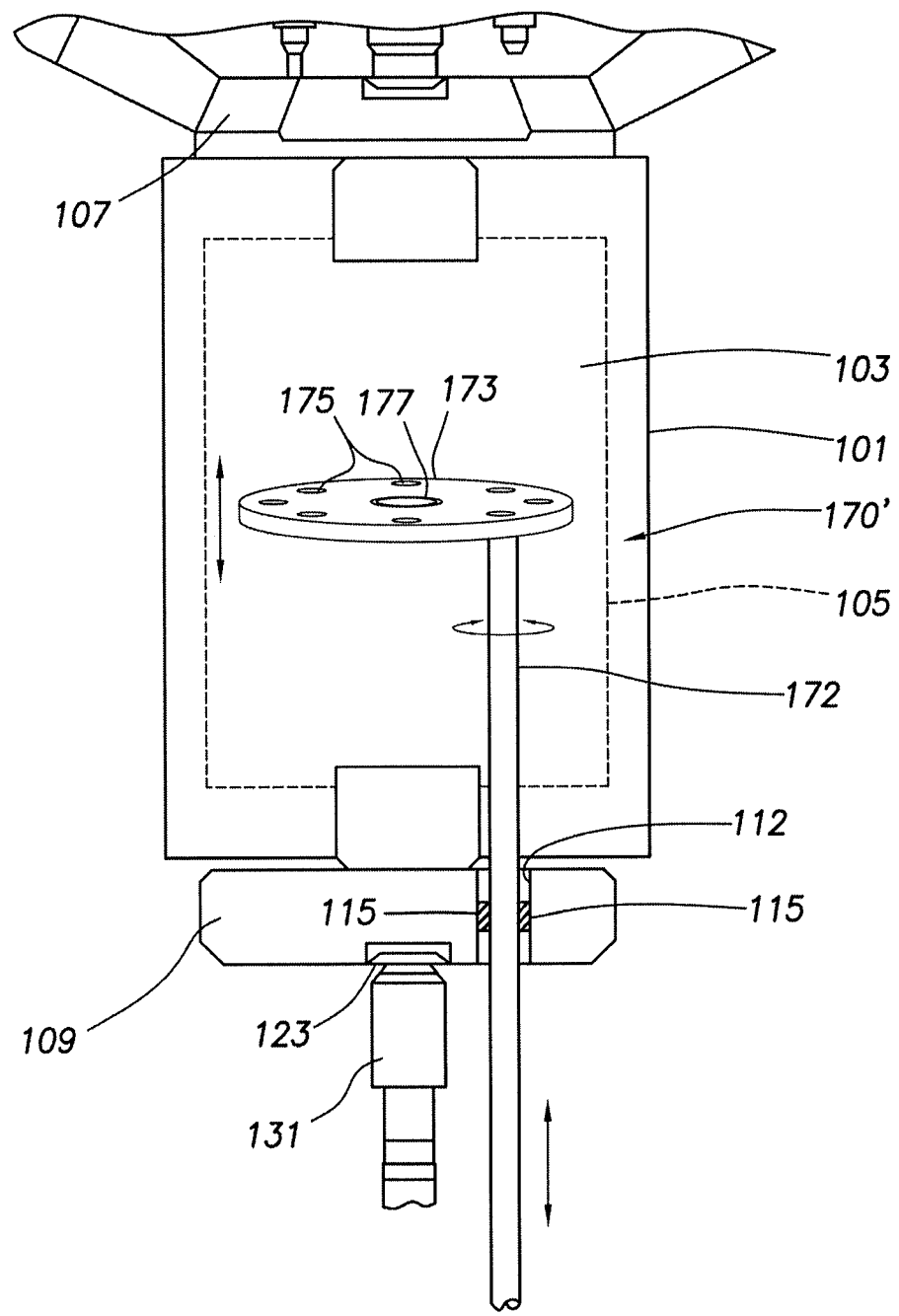
FIG. 1B is a diagram illustrating a portion of the system shown in FIG. 1A with an alternative embodiment of a mixing device in accordance with certain embodiments of the present disclosure.

Referring now to FIG. 1B, a pressure vessel 101' similar to that shown from FIG. 1A is shown, which includes an internal cell 103' defined by cell housing or cylinder wall or vessel wall 105', upper end cap 107', lower end cap 109', and physical contacts 121' and 123'. Pressure vessel 101' also includes a mixing device 170' that includes a rod 172 having one end that extends into the internal cell 103' through an opening 112 in the lower end cap 109'. Seals 115 are also located in the opening 112 that contact both the walls of the opening 112 and the surfaces of the rod 172 such that the lower end of the internal cell 103' is still closed, but rod 172 may shift upward and/or downward as indicated by the arrows shown in FIG. 1B, e.g., with piston-like action, and may rotate around a (vertical) central axis of the rod 172. Mixing device 170' includes a disc 173 coupled to the end of the rod 172 that is disposed in the internal cell 103' such that the surface of the disc 173 is generally perpendicular to the rod 172. Disc 173 also includes several perforations 175 that allow flow of the cement slurry or suspension therethrough. Thus, when the rod 172 and disc 173 of mixing device 170' are moved upward and downward and/or when the rod 172 is rotated, the cement slurry is also moved, agitated, or otherwise mixed. In some embodiments, after the cement slurry has been adequately mixed or conditioned but before measurements are taken, the mixing device 170' may be deactivated and the rod 172 may be moved upward or downward such that the disc 173 is placed just below and adjacent to the upper end cap 107' or just above and adjacent to the lower end cap 109'. The disc 173 also includes an aperture 177 that can be aligned with the physical contact 121' or 123' so that the disc 173 does not interfere with wave transmission between the cement sample in the cell 103' and the physical contact 121' or 123'.

Referring back to FIG. 1A, in certain embodiments, the ultrasonic analysis system 100 optionally may further comprise an information handling system 180. In the embodiment shown in FIG. 1A, the information handling system 180 may be coupled to one or more of the receiver 134, transmitter 140, pressure and heat source 150, and thermocouple 160. Signals received by the receiver 134 indicative of the transit time and/or attenuation of the p-waves through the cell 103 may be transmitted to an information handling system 180, where they can be processed, for example, to calculate one or more properties of the cement composition in the cell 103. In some embodiments, the information handling system 180 also may monitor and/or control the operation of the pressure and heat source 150. The information handling system 180 associated with system 100 could be, for example, wholly contained within the same housing as other components of system 100, located at the same site as the remaining components of the system 100, or may be located at a remote location but still communicatively coupled to one or more other components of the system, e.g., via a wired or wireless connection.

In operating the ultrasonic analysis system of FIG. 1A, acoustic energy waves propagating from lower end cap 109 passes through the cement composition sample in cell 103 to upper end cap 107. In other embodiments of the present disclosure where the connections of the transducer/receiver and the transmitter at the upper and lower ends of the pressure vessel 101 are reversed, the acoustic energy waves may propagate from the upper end cap 107 and pass through the cement composition sample in cell 103 to lower end cap 109. The transit time or velocity of these waves as well as their attenuation and/or intensity may be used to calculate one or more properties of the cement composition. As used herein, "attenuation" refers to the loss of energy in a signal as a wave travels through a medium. In some embodiments, the energy loss may be due to absorption and/or scattering, and also may be due to transition of the signal from one medium to another (for example, when the signal transitions from a metal to a liquid when transmitted into the cement sample, and then transitions from a liquid to a metal when it is received at the other end of the sample). Scattering may be caused by particles suspended in the medium. In certain embodiments, attenuation may depend on environmental factors such as temperature and pressure, as well as the structural make-up of the medium. In certain embodiments, for example, different cement compositions may have completely different attenuation properties from each other. Attenuation also may be frequency dependent, and, in certain situations, higher frequencies may be more attenuated than lower frequencies. In certain embodiments, when attenuation is highly frequency dependent, a frequency-dependent attenuation function may be more accurate than a single attenuation value for all frequencies.

In some embodiments, the acoustic p-waves discussed above may travel through materials other than the cement composition (e.g., metal components of the test apparatus), which may affect the velocity of the waves as measured using the systems disclosed herein. Moreover, the velocity of electrical waves may be affected by the materials and/or structure of the electrical connections through which they travel. In some embodiments, a baseline calibration may be performed and applied to the calculations discussed below in order to account for these effects on the observed velocity of the waves. For example, a steel rod of known composition may be placed between the upper and lower end caps 107 and 109 of the pressure vessel 101 shown in FIG. 1. The measured velocity of acoustic waves that are passed from one of the end caps to the other through the steel rod may be compared to a known value of the velocity of sound waves through steel (e.g., obtained from literature), and the difference between those values can be calculated and considered as offset to account for the aforementioned factors that may affect the observed velocity of p-waves traveling through a cement composition sample. When testing a cement composition sample using that same apparatus, the measurements can be corrected by the offset value calculated in the calibration. Other materials through which the speed of sound waves is known (e.g., distilled water) may be placed in the pressure vessel to perform calibrations that may be applied to measurements of waves passing through a cement composition.

The velocity of the p-waves having relatively high and low frequencies ($V_f$ and $V_s$, respectively) transmitted through the cement composition samples may be used to calculate one or more properties of the cement composition according to the equations and techniques described below. An example of a process 200 according to certain embodiments of the present disclosure for calculating these properties that uses the equations discussed below is illustrated in the flowchart provided in FIG. 2. The measurements and steps of that process may be performed at one or more times as the cement composition sample hydrates, or may be performed substantially continuously throughout the hydration process. In some embodiments, the calculations described below may be made in real time as the p-waves waves traveling through the cement composition are monitored. As one of skill in the art with the benefit of this disclosure will recognize, certain of the equations below and the theories from which they are derived may depend on certain assumptions. For example, certain of the equations discussed below may assume that viscous forces in the cement composition samples will substantially lock fluid and solid particulate motion therein. For particular applications of the present invention, these and/or other assumptions may not be applicable and/or different theories may apply, and thus these equations may be modified, or different equations may be used, accordingly in calculating properties of the cement composition under those circumstances. Moreover, one or more of the calculations described below may be performed by using an information handling system such as those described above.

Figure 2:
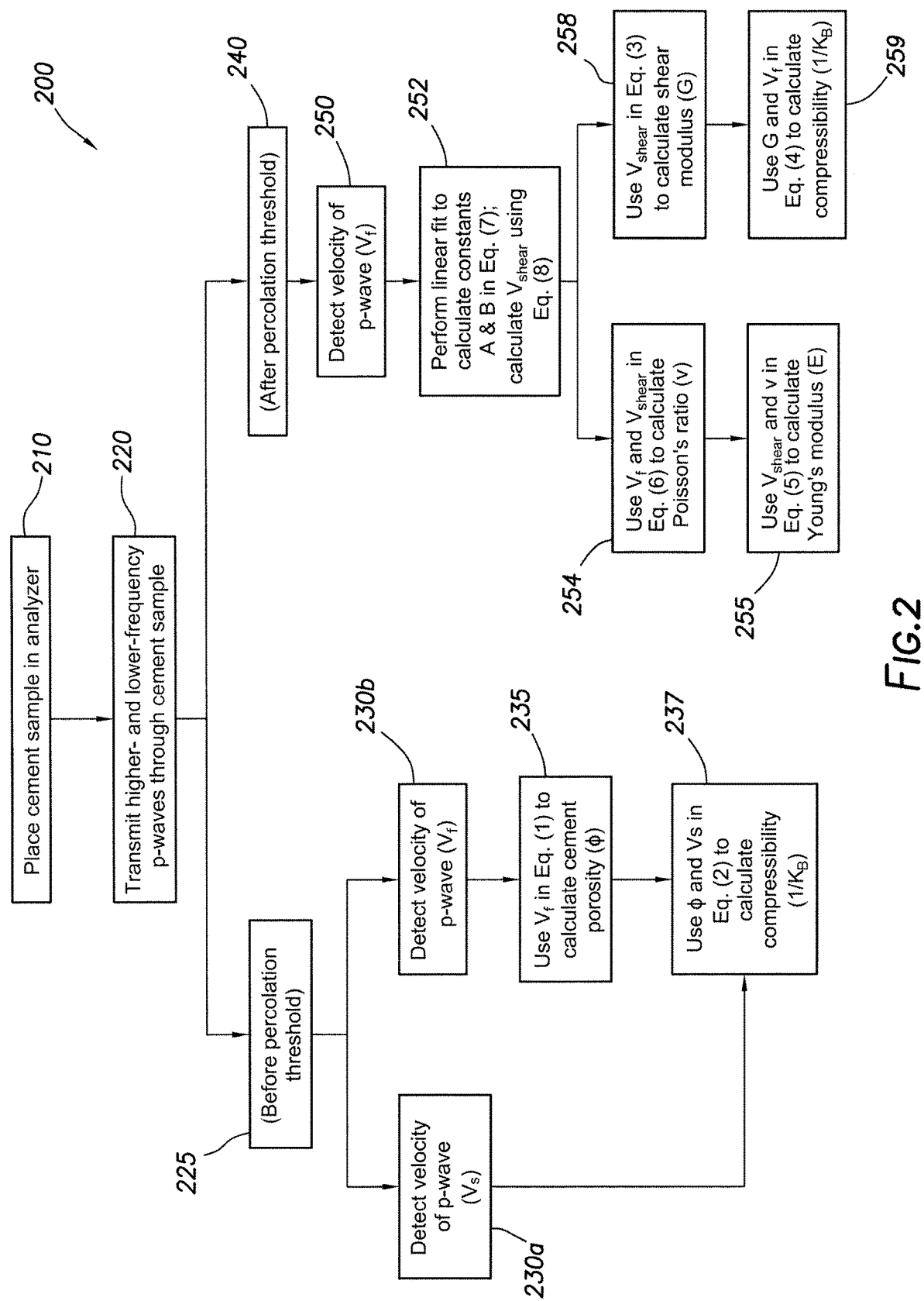
FIG. 2 is a flowchart illustrating an example of a method of determining various properties of a cement composition in accordance with certain embodiments of the present disclosure.

Referring now to FIG. 2, process 200 begins at step 210 by placing the cement composition sample in the ultrasonic analysis system, such as the system illustrated in FIG. 1A. In some embodiments, the cement composition sample may have been conditioned (e.g., stirred or agitated) prior to placement in the system at step 210. In other embodiments, the sample may be conditioned after it is placed in the system using a mixing device integrated into the ultrasonic analysis system for a period of time before the process 200 continues. Once any such optional conditioning of the cement has been performed, at step 220, the pressure vessel may be brought to the appropriate temperature and pressure conditions (e.g., the temperature and pressure of the region of a well bore or subterranean formation where the cement composition is intended to be used), and the ultrasonic transmitter may begin transmitting p-waves having relatively high and low frequencies through the cement composition sample. Under Biot's theory, p-waves having both high and low frequencies will travel through the cement composition before the cement composition reaches its percolation threshold (e.g., while the cement composition behaves as a slurry, suspension, or in its weak frame limit), and thus the velocities of those p-waves through the cement composition sample may be monitored at steps 230a and 230b during this period (step 225). During this period, $V_f$ may be expressed as a function of the porosity of the cement composition sample ($\phi$) according to Equation (1):

$$V_f = \left( \frac{\left( \frac{1-\phi}{K_s} + \frac{\phi}{K_f} \right)^{-1}}{[(1-\phi)\rho_s + \phi\rho_f]} \right)^{0.5} \tag{1}$$

wherein $K_s$ is the weighted average (e.g., by concentration) bulk modulus of solid constituents of the cement composition, $K_f$ is the bulk modulus of the fluid in the cement composition (e.g., water and other liquid additives together), $\rho_s$ is the weighted average density of solid constituents of the cement composition, and $\rho_f$ is the density of the fluid in the cement composition (e.g., water and other liquid additives together). Similarly, $V_s$ may be expressed as a function of the porosity of the cement composition, the bulk modulus of the cement composition ($K_b$), and the shear modulus of the composition (G) according to Equation (2):

$$V_s = \left( \frac{K_b + \frac{4}{3}G}{[(1-\phi)\rho_s + (\phi - 2 + \alpha/\phi)\rho_f]} \right)^{0.5} \tag{2}$$

wherein $\alpha$ is a geometric factor and related to $\phi$ as $\alpha = \frac{1}{2}(1 + 1/\phi)$. Moreover, before the cement composition reaches its percolation threshold, the cement is in its weak frame limit, and G may approach zero. Thus, $V_f$ may be used with Equation (1) to calculate the porosity of the cement composition ($\phi$) at step 235, and $\phi$ and $V_s$ may be used with Equation (2) at step 237 to calculate the bulk modulus ($K_b$) and compressibility (1/$K_b$) of the cement composition.

Once the cement composition sample reaches its percolation threshold at step 240, only the p-wave having a relatively higher frequency will be transmitted through the composition for detection at step 250, and thus various mechanical properties of the composition may be related to $V_f$ based on Equations (3) through (6):

$$G = V_{shear}^2 \rho \tag{3}$$

$$K_b = V_f^2 \rho + \frac{4}{3}G \tag{4}$$

$$E = 2V_{shear}^2 \rho(1 + v) \tag{5}$$

$$v = \frac{1}{2} \left[ \frac{\left( \frac{V_f}{V_{shear}} \right)^2 - 2}{\left( \frac{V_f}{V_{shear}} \right)^2 - 1} \right] \tag{6}$$

wherein E is the Young's modulus of the composition, v is the Poisson's ratio of the composition, G is the shear modulus of the composition, $K_b$ is the bulk modulus of the composition, $V_{shear}$ is the velocity of a shear wave through the cement composition, and $\rho$ is the density of the cement composition. In some embodiments, $\rho$ for the cement composition may be measured, while the cement composition is in the sample cell of the ultrasonic analysis system or a different apparatus or system. In absence of measured value, a calculated average density may be used since the absolute change in density of the cement composition typically is not large, and thus any resulting errors in calculation of mechanical properties based on this average density would be small or negligible. Once the cement composition has reached its percolation threshold, p-waves and shear waves are transmitted substantially due to the motion of the solid matrix of the cement composition, making the role of fluid motion in the composition less significant. Based on that assumption, the shear modulus (G) of the cement composition may have a linear relationship to $V_f$, as shown in Equation 7:

$$G = AV_f + B \tag{7}$$

wherein A and B are numerical constants specific to the particular cement composition of interest.

Figure 3:
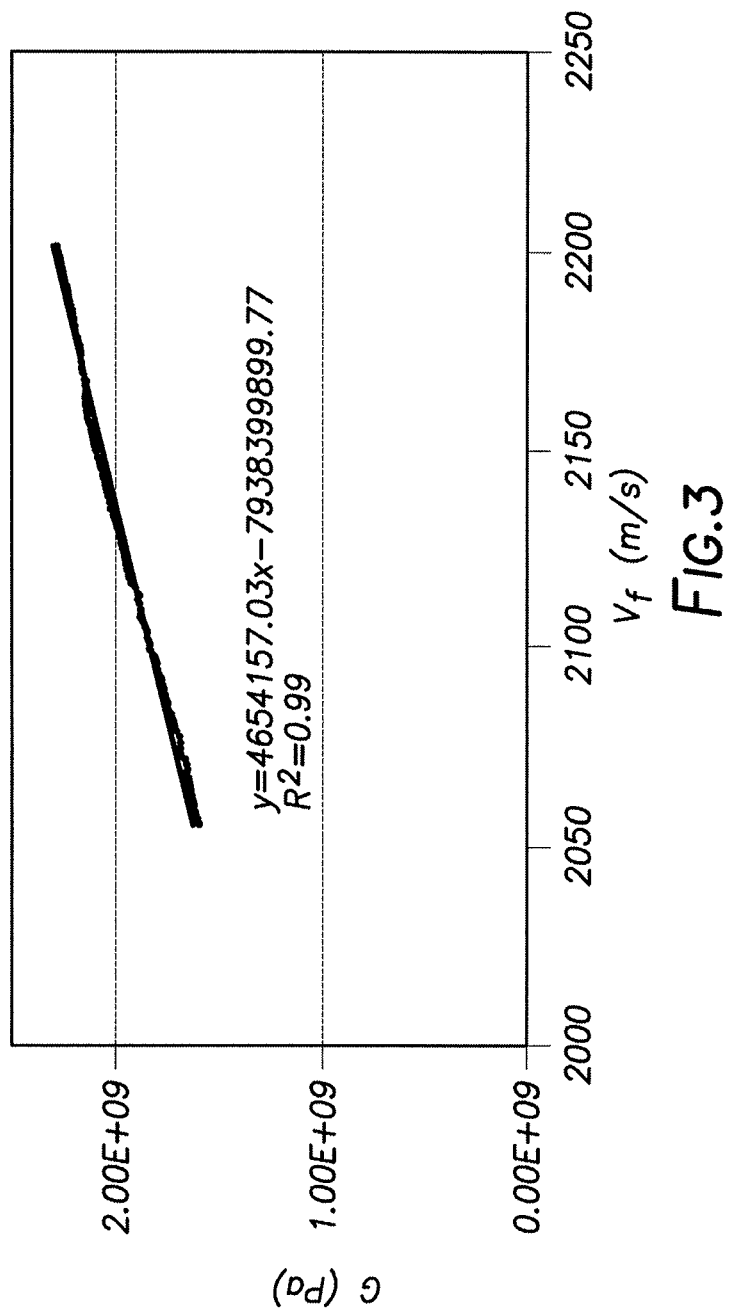
FIG. 3 is a graph showing data relating to the shear modulus of a cement composition (G) versus the velocity of a compression wave ($V_p$) through the cement composition in accordance with certain embodiments of the present disclosure.

The values of A and B for a particular cement composition may be obtained from literature or previously-determined values, or may be calculated by performing a linear regression of data for the shear modulus of the cement composition (G) and velocity of a compression wave or p-wave ($V_f$) through the cement composition, as shown at step 252. FIG. 3 is a plot of data and an extrapolated line of best fit from an example of a linear regression analysis that was performed for an example of a cement composition comprising a class G cement having a density of 15.8 pounds per gallon (ppg) using a Mechanical Properties Analyzer (MPro) system. Based on the linear equation obtained in that analysis, the value of A was roughly 4.65 and the value of B was roughly 7.94. The $R^2$ value of 0.99 confirmed the mathematical relationship between G and $V_f$ in Equation (7).

Because the motion of a shear wave through the cement composition would substantially involve only the motion of the solid matrix of the composition, $V_f$ and $V_{shear}$ may be related based on the combination and rearrangement of Equations (3) and (7), and $V_{shear}$ may be calculated once the values A and B are obtained using Equation (8):

$$V_{shear} = \sqrt{\frac{AV_f + B}{\rho}} \qquad (8)$$

$V_{shear}$ then may be used in Equations (3) through (6) above to calculate the Poisson's ratio (step 254), Young's modulus (step 255), shear modulus (step 258), and compressibility ($1/K_b$) (step 259) of the cement composition. Thus, in some embodiments, these properties may be calculated without actually observing or measuring $V_{shear}$. As a person of skill in the art will recognize with the benefit of this disclosure, the values of these properties calculated in this manner may require application of a correlation constant in order to be converted or compared to their static or mechanical equivalents.

As noted above, the ultrasonic analysis systems of the present disclosure may be configured to detect or monitor the amplitude of waves traveling through the cement composition sample. In some embodiments, the amplitude of the p-waves may be monitored before and/or after the percolation threshold is reached during the process illustrated in FIG. 2. In some embodiments, the amplitude of the p-waves may be used to determine when the cement composition sample has reached its percolation threshold, which may determine the appropriate time and manner for calculating certain of the properties discussed above. In some embodiments, the amplitude of the p-waves optionally may be used to determine the sonic gel strength of the cement composition sample before and/or after the percolation threshold has been reached. As a cement composition hydrates and its gel strength increases, an ultrasonic p-wave may attenuate in accordance with certain mathematical relationships with gel strength. The appropriate mathematical relationships for a given cement composition may be determined by testing samples of the cement composition using a process involves high speed sampling of the signal through the cement sample, fast Fourier transform (FFT) analysis, and calculation of intermediate signal attenuation values. Once this process is complete, each attenuation value may transmitted to an information handling system. This attenuation is compared to mechanically measured static gel strength to obtain a mathematical correlation. calculates sonic gel strength values as a function of time. Once this mathematical correlation of attenuation and gel strength is obtained, the gel strength of the cement composition sample may be calculated by monitoring the amplitude of p-waves traveling through the cement and applying that data to the mathematical correlation. The equivalent gel strength thus obtained using sonic means may be referred to as the sonic gel strength.

In some embodiments, the ultrasonic analysis system of the present disclosure optionally may be configured to characterize the compressive strength of the cement composition sample based at least in part on the velocity of the p-wave having a relatively higher frequency transmitted through the cement composition. This may be accomplished using known mathematical relationships between the velocity of the p-wave and compressive strength similar to those used in conventional ultrasonic cement analyzer systems.

In some embodiments, the ultrasonic analysis system of the present disclosure optionally may be configured to determine the change in volume of a cement composition sample during the hydration process. In some embodiments, the cell containing the cement composition sample during the evaluation process is maintained as a closed system in isochoric mode in communication with a known, fixed amount of an inert gas (such as Nitrogen, Argon, Xenon, etc.) in a fixed volume cavity. Since the gas will behave according to the ideal gas law, under isothermal conditions, the initial/final pressures of the gas $P_i$ and $P_f$ and initial/final volumes of the gas $X_i$ and $X_f$, will be related according to Equation (9):

$$P_i X_i = P_f X_f \qquad (9)$$

The pressure of the gas is measured at the start and at the end of the cement hydration process, and thus the final volume of the gas may be calculated using Equation (9). The change in volume of the gas during the cement hydration process then may be used to determine the change in volume of the cement. The change in volume of the cement composition over time also may be calculated by monitoring the pressure of the gas either substantially continuously or at various intervals during the hydration process. If temperature variations occur between the pressure measurements, appropriate corrections can be made before calculating the hydration volume change of the cement.

Figure 4:
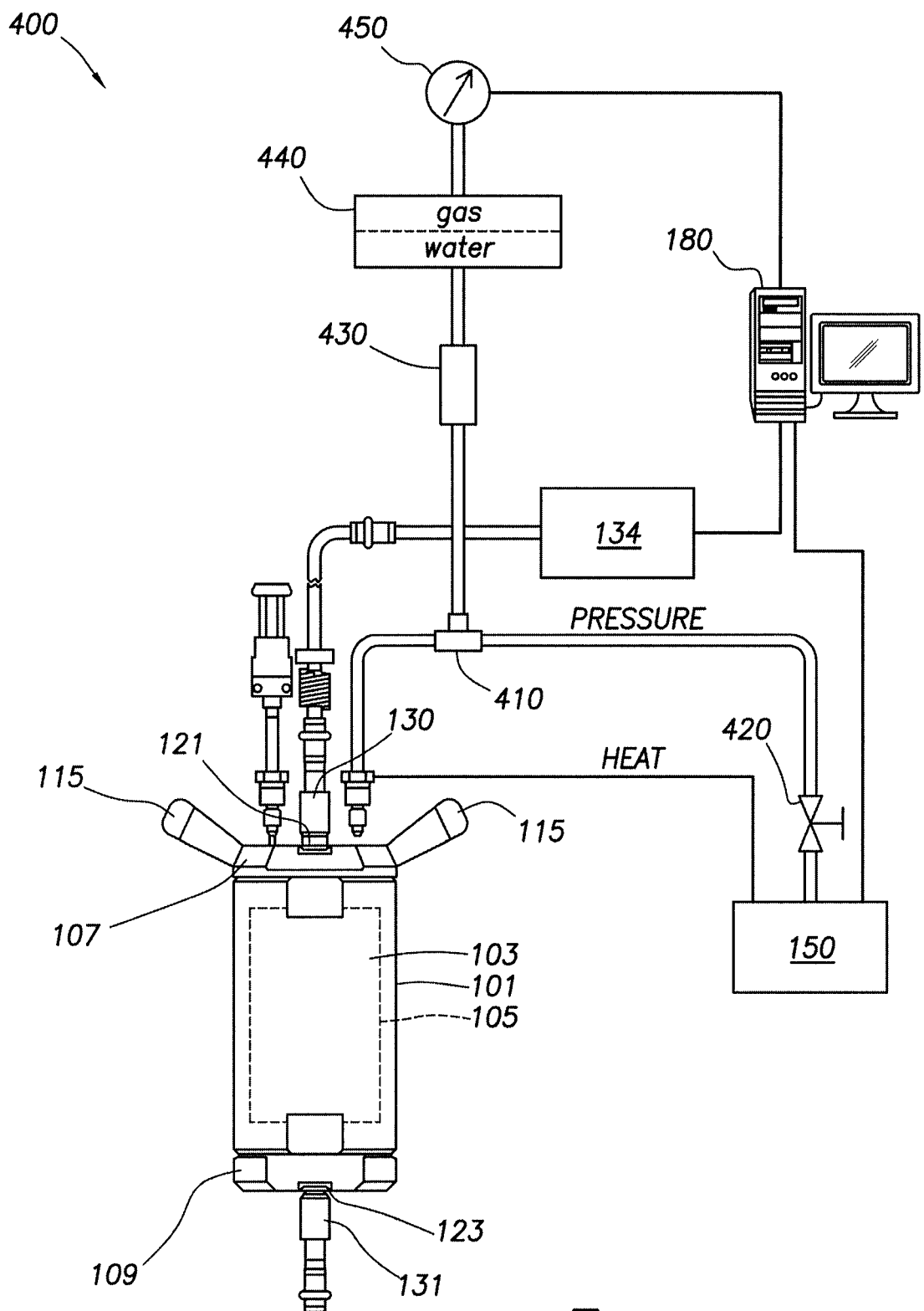
FIG. 4 is a diagram illustrating an example of another ultrasonic analysis system that may be used in accordance with certain embodiments of the present disclosure.

FIG. 4 is a diagram illustrating an example of an ultrasonic analysis system that may be used in accordance with certain embodiments of the present disclosure to determine the change in volume of a cement composition sample during the hydration process. Referring now to FIG. 4, the system 400 includes similar components in a similar configuration as illustrated and described with regard to FIG. 1A. In some embodiments, the pressure vessel 101 in FIG. 4 may be modified to include the alternative mixing device 170' shown in FIG. 1B. The flow line that couples the pressure and heat source 150 to the pressure vessel 101 is fitted with a T-joint 410 that provides an additional flow line coupled to a collar gland fitting 440 through a filter 430. The flow line coupled to the pressure and heat source is also fitted with a needle valve 420 regulates gas flow to the pressure and heat source 150. The collar glad fitting 440 contains the fixed amount of nitrogen gas and water, and is coupled to a pressure transducer 450, which in turn may be coupled to the information handling system 180 or other system for monitoring the pressure. Once pressure within the pressure vessel 101 is built to the desired level using the pressure source 150, needle valve 420 is closed to isolate the pressure vessel with the other components of the system. As the cement hydrates, the change in volume of the cement will consume the water in collar gland fitting 440, which will cause the nitrogen gas therein to expand. This expansion will decrease the pressure in collar gland fitting 440, which will be detected at pressure transducer 450, and a signal indicative of that pressure may be sent to information handling system 180 for use in calculating the corresponding change in the volume of the cement as described above.

In other embodiments, the change in volume of the cement during hydration may be determined by maintaining the vessel or cavity containing the cement composition sample at a constant pressure and measuring the volume of liquid flowing into or out of the vessel or cavity (e.g., through a pump or valve) while or after the cement composition hydrates. The volume of this liquid would indicate the volume change of the cement during the hydration process.

The methods and systems of the present disclosure may be used to evaluate any type of hydratable cement composition that is suitable for use in a subterranean cementing operation. Examples of cement compositions that may be evaluated include, but are not limited to, Portland cements, pozzolanic cement, gypsum cement, high alumina content cement, silica cement, high alkalinity cement, low-density cements, magnesium phosphate cement, and any combination thereof.

In some embodiments, one or more components of the systems shown in FIGS. 1A, 1B, and 4 and/or one or more steps of the process illustrated in FIG. 2, or the entireties of those systems and methods, may be provided or performed at a well site (e.g., at the surface in a service vehicle or mobile laboratory structure) where cementing operations may be performed using a cement composition evaluated using the methods and systems of the present disclosure.

In some embodiments, the methods and systems of the present disclosure, or portions thereof, may be configured to be performed and/or placed within at least a portion of a well bore and/or subterranean formation, among other reasons, to evaluate the properties of a cement composition while it is in that location and subjected to downhole conditions. In some embodiments, a downhole tool comprising an ultrasonic transducer may be placed in a portion of a subterranean formation (e.g., in a well bore) where the transducer may emit and receive p-waves of high and low frequencies that pass through at least a portion of a cement composition residing therein. In these embodiments, the transducer may comprise a set of one or more transmitters and a set of one or more receivers that emits and receives the p-waves in a manner similar to the operation of the transducers in the ultrasonic analysis system shown in FIG. 1A and described above. In these embodiments, the pressure and heat source 150 may not be required, since the elevated temperature and/or pressure conditions already may be present in the subterranean environment. In some embodiments, the ultrasonic transducers in the downhole tool may be coupled to other pieces of control and/or analysis equipment (e.g., an information handling system, etc.) that are used to control, monitor, or process data from the transducers.

In some embodiments, such a tool may be positioned inside a tubing or casing that has been cemented in a well bore by a cement composition that has been pumped into an annulus between the outer wall of the tubing or casing and the wall of the well bore. The p-waves emitted by the transmitter may travel in an outward radial direction through the cement toward the well bore wall, and may be reflected off the well bore wall and back through the cement to the receivers. Measurements of those reflected p-waves taken at the receivers may be used as described above to determine one or more properties of the cement composition. In some embodiments, the p-waves may be reflected back to the receiver off of, among other things, other fluids present in the well bore and/or other structures before the p-waves pass through the cement composition, which may hinder the determination of properties of the cement composition itself. However, the known distances between the tool and the cement and/or well bore wall and the known composition of the fluids present in the formation and/or tubing can be used to determine whether the waves being received were reflected before passing through the cement composition. If so, those waves may be ignored in determining the properties of the cement composition, and the delayed reflections may be used in determining properties of the cement composition.

The properties of the cement composition samples measured using the methods and systems described above may be used in selecting a cement composition appropriate for use in certain subterranean cementing operations in which the selected cement composition is pumped into at least a portion of a well bore penetrating a portion of a subterranean formation and allowed to at least partially set therein. Those cement compositions selected using the methods and systems of the present disclosure may directly or indirectly affect one or more components or pieces of equipment associated with the preparation, delivery, recapture, recycling, reuse, and/or disposal of the cement compositions.

For example, the cement compositions may directly or indirectly affect one or more mixers, related mixing equipment, mud pits, storage facilities or units, composition separators, heat exchangers, sensors, gauges, pumps, compressors, and the like used generate, store, monitor, regulate, and/or recondition the cement compositions. The cement compositions may also directly or indirectly affect any transport or delivery equipment used to convey the cement compositions to a well site or downhole such as, for example, any transport vessels, conduits, pipelines, trucks, tubulars, and/or pipes used to compositionally move the cement compositions from one location to another, any pumps, compressors, or motors (e.g., topside or downhole) used to drive the cement compositions into motion, any valves or related joints used to regulate the pressure or flow rate of the cement compositions, and any sensors (e.g., pressure and temperature), gauges, and/or combinations thereof, and the like. The cement compositions may also directly or indirectly affect the various downhole equipment and tools that may come into contact with the cement compositions/additives such as, but not limited to, wellbore casing, wellbore liner, completion string, insert strings, drill string, coiled tubing, slickline, wireline, drill pipe, drill collars, mud motors, downhole motors and/or pumps, cement pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like.

Figure 5:
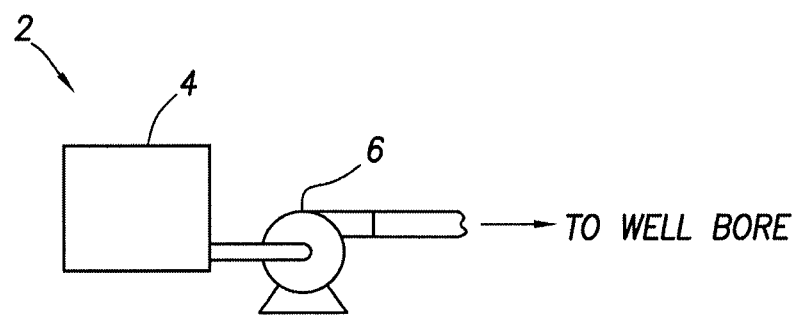
FIG. 5 illustrates a system for preparation and delivery of a cement composition to a well bore in accordance with aspects of the present disclosure.

Referring now to FIG. 5, a system that may be used in the preparation of a cement composition in accordance with example embodiments will now be described. FIG. 5 illustrates a system 2 for preparation of a cement composition and delivery to a well bore in accordance with certain embodiments. As shown, the cement composition may be mixed in mixing equipment 4, such as a jet mixer, re-circulating mixer, or a batch mixer, for example, and then pumped via pumping equipment 6 to the well bore. In some embodiments, the mixing equipment 4 and the pumping equipment 6 may be disposed on one or more cement trucks as will be apparent to those of ordinary skill in the art. In some embodiments, a jet mixer may be used, for example, to continuously mix the composition, including water, as it is being pumped to the well bore.

Figure 6A:
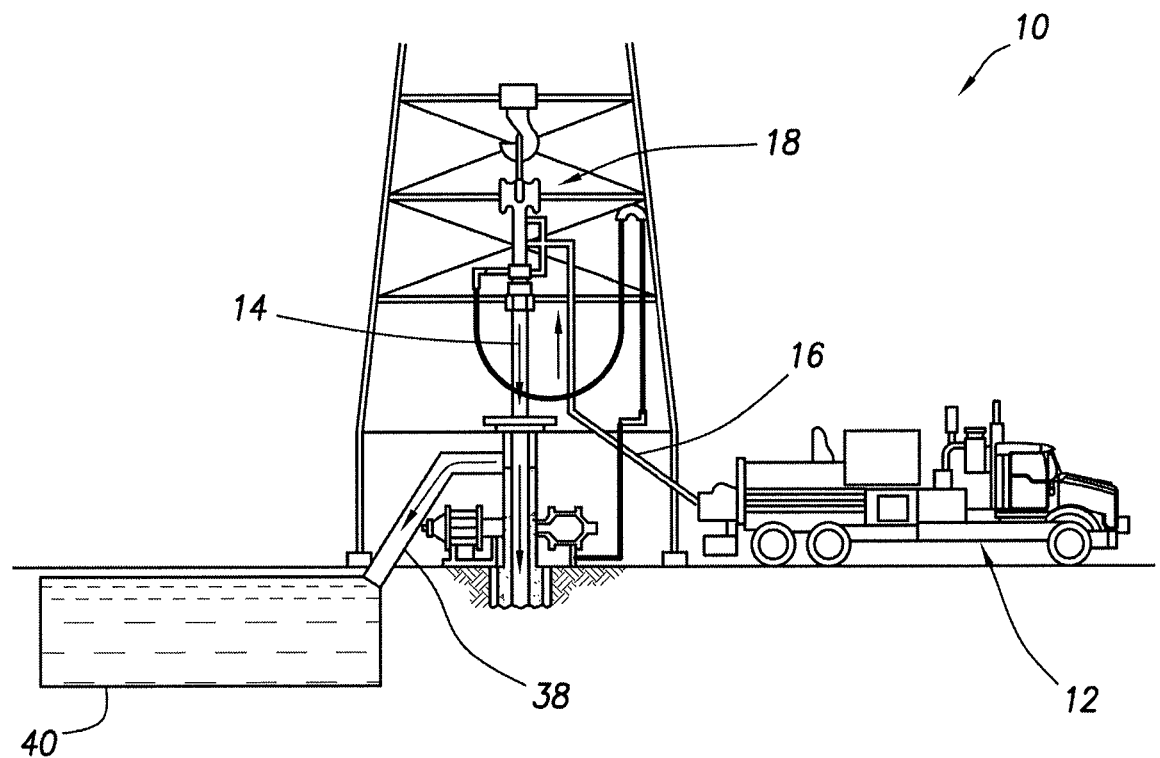
FIG. 6A illustrates surface equipment that may be used in placement of a cement composition in a well bore in accordance with aspects of the present disclosure.

An example technique and system for placing a cement composition into a subterranean formation will now be described with reference to FIGS. 6A and 6B. FIG. 6A illustrates surface equipment 10 that may be used in placement of a cement composition in accordance with certain embodiments. It should be noted that while FIG. 6A generally depicts a land-based operation, those skilled in the art will readily recognize that the principles described herein are equally applicable to subsea operations that employ floating or sea-based platforms and rigs, without departing from the scope of the disclosure. As illustrated by FIG. 6A, the surface equipment 10 may include a cementing unit 12, which may include one or more cement trucks. The cementing unit 12 may include mixing equipment 4 and pumping equipment 6 (e.g., FIG. 5) as will be apparent to those of ordinary skill in the art. The cementing unit 12 may pump a cement composition 14 through a feed pipe 16 and to a cementing head 18 which conveys the cement composition 14 downhole.

Figure 6B:
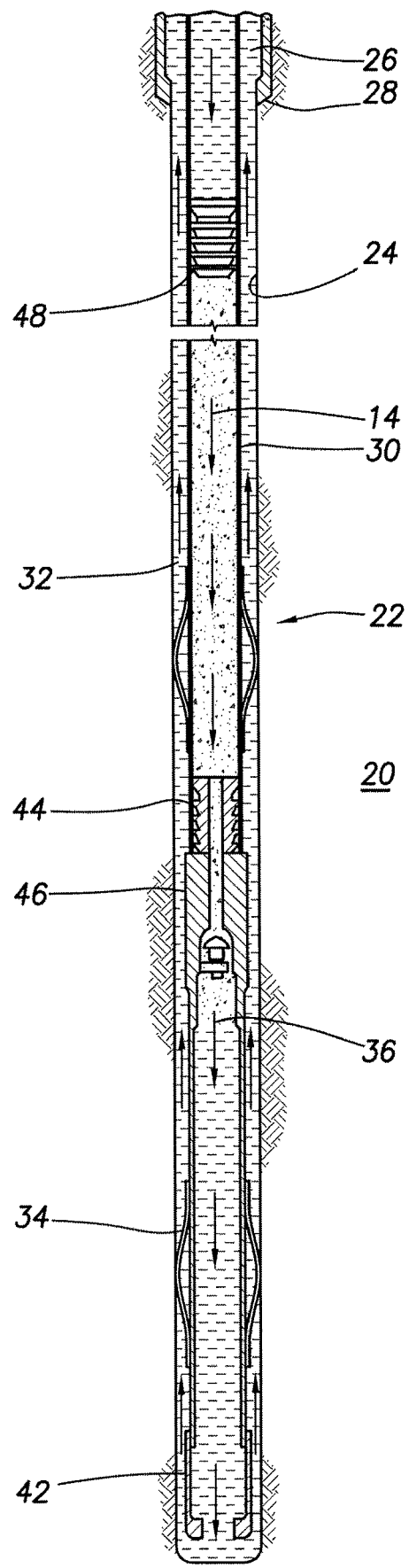
FIG. 6B illustrates placement of a cement composition into a well bore annulus in accordance with aspects of the present disclosure.

Turning now to FIG. 6B, the cement composition 14 may be placed into a subterranean formation 20 in accordance with example embodiments. As illustrated, a well bore 22 may be drilled into the subterranean formation 20. While well bore 22 is shown extending generally vertically into the subterranean formation 20, the principles described herein are also applicable to well bores that extend at an angle through the subterranean formation 20, such as horizontal and slanted well bores. As illustrated, the well bore 22 comprises walls 24. In the illustrated embodiments, a surface casing 26 has been inserted into the well bore 22. The surface casing 26 may be cemented to the walls 24 of the well bore 22 by cement sheath 28. In the illustrated embodiment, one or more additional conduits (e.g., intermediate casing, production casing, liners, etc.) shown here as casing 30 may also be disposed in the well bore 22. As illustrated, there is a well bore annulus 32 formed between the casing 30 and the walls 24 of the well bore 22 and/or the surface casing 26. One or more centralizers 34 may be attached to the casing 30, for example, to centralize the casing 30 in the well bore 22 prior to and during the cementing operation.

With continued reference to FIG. 6B, the cement composition 14 may be pumped down the interior of the casing 30. The cement composition 14 may be allowed to flow down the interior of the casing 30 through the casing shoe 42 at the bottom of the casing 30 and up around the casing 30 into the well bore annulus 32. The cement composition 14 may be allowed to set in the well bore annulus 32, for example, to form a cement sheath that supports and positions the casing 30 in the well bore 22. While not illustrated, other techniques may also be utilized for introduction of the cement composition 14. By way of example, reverse circulation techniques may be used that include introducing the cement composition 14 into the subterranean formation 20 by way of the well bore annulus 32 instead of through the casing 30.

As it is introduced, the cement composition 14 may displace other fluids 36, such as drilling fluids and/or spacer fluids, that may be present in the interior of the casing 30 and/or the well bore annulus 32. At least a portion of the displaced fluids 36 may exit the well bore annulus 32 via a flow line 38 and be deposited, for example, in one or more retention pits 40 (e.g., a mud pit), as shown on FIG. 6A. Referring again to FIG. 6B, a bottom plug 44 may be introduced into the well bore 22 ahead of the cement composition 14, for example, to separate the cement composition 14 from the fluids 36 that may be inside the casing 30 prior to cementing. After the bottom plug 44 reaches the landing collar 46, a diaphragm or other suitable device ruptures to allow the cement composition 14 through the bottom plug 44. In FIG. 6B, the bottom plug 44 is shown on the landing collar 46. In the illustrated embodiment, a top plug 48 may be introduced into the well bore 22 behind the cement composition 14. The top plug 48 may separate the cement composition 14 from a displacement fluid 50 and also push the cement composition 14 through the bottom plug 44.

An embodiment of the present disclosure is a method comprising: providing a cement composition in a sample cell; before the cement composition reaches a percolation threshold, transmitting at least a first p-wave having a first frequency and a second p-wave having a second frequency through the cement composition while allowing the cement composition to at least partially hydrate, wherein the first frequency is higher than the second frequency; determining a velocity of the first p-wave through the sample and a velocity of the second p-wave through the cement composition; after the cement composition reaches the percolation threshold, transmitting at least a third p-wave having a third frequency through the cement composition while allowing the cement composition to at least partially hydrate, wherein the third frequency is higher than the second frequency; determining at least a velocity of the third p-wave through the cement composition; based at least in part on the velocities of the first p-wave and the second p-wave, determining a first compressibility of the cement composition ($1/K_B$); and based at least in part on the velocity of the third p-wave, determining a Poisson's ratio of the cement composition (v), a Young's modulus of the cement composition (E), a shear modulus of the cement composition (G), and a second compressibility ($1/K_b$) of the cement composition.

Another embodiment of the present disclosure is a system comprising: a pressure vessel comprising one or more walls that define a sample cell; a source of pressure for increasing or decreasing pressure within the pressure vessel; an ultrasonic transmitter disposed near a first end of the sample cell; an ultrasonic transducer disposed near a second end of the sample cell that is opposite the first end; wherein: the ultrasonic transmitter is configured to transmit at least a first plurality of p-waves having a first frequency and a second plurality of p-waves having a second frequency through the sample cell, wherein the first frequency is higher than the second frequency; and the ultrasonic transducer is configured to detect at least the first and second pluralities of p-waves.

Another embodiment of the present disclosure is a method comprising: providing a cement composition in a sample cell; before the cement composition reaches a percolation threshold, transmitting at least a first p-wave having a first frequency and a second p-wave having a second frequency through the cement composition while allowing the cement composition to at least partially hydrate, wherein the first frequency is higher than the second frequency; determining a velocity of the first p-wave through the sample and a velocity of the second p-wave through the cement composition; after the cement composition reaches the percolation threshold, transmitting at least a third p-wave having a third frequency through the cement composition while allowing the cement composition to at least partially hydrate, wherein the third frequency is higher than the second frequency; determining at least a velocity of the third p-wave through the cement composition; calculating a first compressibility of the cement composition ($1/K_b$) before its percolation threshold according to a formula:

$$V_s = \left( \frac{K_b + \frac{4}{3}G}{\left[(1-\phi)\rho_s + \left(\phi - 2 + \frac{\alpha}{\phi}\right)\rho_f\right]} \right)^{0.5}$$

wherein $V_s$ is the velocity of the second p-wave through the cement composition, $\phi$ is a porosity of the cement composition, $\alpha$ is a geometric factor and is related to $\phi$ as $\alpha=\frac{1}{2}(1+1)$, $\rho_s$ is a weighted average density of solid constituents of the cement composition, $\rho_f$ is a density of one or more fluid components of the cement composition, and G approaches zero; calculating a Poisson's ratio of the cement composition (v) using the formula:

$$v = \frac{1}{2}\left[\frac{\left(\frac{V_f}{V_{shear}}\right)^2 - 2}{\left(\frac{V_f}{V_{shear}}\right)^2 - 1}\right]$$

wherein $V_f$ is the velocity of the third p-wave and $V_{shear}$ is a velocity of a shear wave through the cement composition; calculating a Young's modulus of the cement composition (E) using the formula:

$E = 2V_{shear}^2 \rho(1+v)$ wherein $\rho$ is a density of the cement composition; calculating a shear modulus of the cement composition (G) using the formula:

$G = V_{shear}^2 \rho$ calculating a second compressibility ($1/K_b$) of the cement composition after its percolation threshold using the formula:

$$K_b = V_f^2 \rho + \frac{4}{3}G$$

determining an attenuation of one or more of the first p-wave and the third p-wave that has been transmitted through the cement composition; based at least in part on the attenuation of the first p-wave or third p-wave, determining a sonic gel strength of the cement composition; providing a fixed amount of an inert gas in a cavity in communication with the sample cell; measuring an initial pressure of the inert gas within the cavity; measuring a second pressure of the inert gas within the cavity after the cement composition has been allowed to at least partially hydrate; and based at least in part on the initial pressure and the second pressure of the inert gas, calculating a change in volume of the cement composition that has been allowed to at least partially hydrate.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The indefinite articles "a" or "an," as used in the claims, are defined herein to mean one or more than one of the element that it introduces. Also, the terms in the claims have their plain, ordinary meaning unless otherwise explicitly and clearly defined by the patentee.

What is claimed is:

1. A method comprising:
   providing a cement composition in a sample cell;
   before the cement composition reaches a percolation threshold,
      transmitting at least a first p-wave having a first frequency and a second p-wave having a second frequency through the cement composition while allowing the cement composition to at least partially hydrate, wherein the first frequency is higher than the second frequency;
      determining a velocity of the first p-wave through the sample and a velocity of the second p-wave through the cement composition;
   after the cement composition reaches the percolation threshold,
      transmitting at least a third p-wave having a third frequency through the cement composition while allowing the cement composition to at least partially hydrate, wherein the third frequency is higher than the second frequency;
      determining at least a velocity of the third p-wave through the cement composition;
   based at least in part on the velocities of the first p-wave and the second p-wave, determining a first compressibility of the cement composition ($1/K_B$); and
   based at least in part on the velocity of the third p-wave, determining a Poisson's ratio of the cement composition (v), a Young's modulus of the cement composition (K), a shear modulus of the cement composition (G), and a second compressibility ($1/K_b$) of the cement composition.

2. The method of claim 1 further comprising:
   based at least in part on one or more of the Poisson's ratio of the cement composition, the Young's modulus of the cement composition, the shear modulus of the cement composition, the first compressibility of the cement composition, and the second compressibility of the cement composition, selecting a downhole cementing fluid for use in an operation in a subterranean formation, wherein the downhole cementing fluid comprises one or more of the same components as the cement composition; and
   introducing the downhole cementing fluid into at least a portion of the subterranean formation.

3. The method of claim 1 further comprising:
  determining an attenuation of one or more of the first p-wave and the third p-wave that has been transmitted through the cement composition; and
  based at least in part on the attenuation of the first p-wave or third p-wave, determining a sonic gel strength of the cement composition.

4. The method of claim 1 further comprising:
  providing a fixed amount of an inert gas in a cavity in communication with the sample cell;
  measuring an initial pressure of the inert gas within the cavity;
  measuring a second pressure of the inert gas within the cavity after the cement composition has been allowed to at least partially hydrate;
  based at least in part on the initial pressure and the second pressure of the inert gas, determining a change in volume of the cement composition that has been allowed to at least partially hydrate.

5. The method of claim 1 wherein:
  the Poisson's ratio of the cement composition, the Young's modulus of the cement composition, the shear modulus of the cement composition, the first compressibility of the cement composition, and the second compressibility of the cement composition are determined using an information handling system; and
  the information handling system receives one or more signals indicative of or used to determine the velocities of the first p-wave, the second p-wave, and the third p-wave.

6. The method of claim 1 wherein the frequencies of the first p-wave and the third p-wave are from about 400 kHz to about 1000 kHz, and the frequency of the second p-wave is from about 30 kHz to about 400 kHz.

7. The method of claim 1 wherein the frequencies of the first p-wave and the third p-wave are from about 600 kHz to about 800 kHz, and the frequency of the second p-wave is from about 50 kHz to about 200 kHz.

8. The method of claim 1 further comprising, based at least in part on the velocity of the third p-wave, determining a compressive strength of the cement composition.

9. The method of claim 1 wherein the cement composition comprises at least one cementitious material selected from the group consisting of a Portland cement, a pozzolanic cement, a gypsum cement, a high alumina content cement, a silica cement, a high alkalinity cement, a low-density cement, a magnesium phosphate cement, and any combination thereof.

10. A method comprising:
  providing a cement composition in a sample cell;
  before the cement composition reaches a percolation threshold,
    transmitting at least a first p-wave having a first frequency and a second p-wave having a second frequency through the cement composition while allowing the cement composition to at least partially hydrate, wherein the first frequency is higher than the second frequency;
    determining a velocity of the first p-wave through the sample and a velocity of the second p-wave through the cement composition;
  after the cement composition reaches the percolation threshold,
    transmitting at least a third p-wave having a third frequency through the cement composition while allowing the cement composition to at least partially hydrate, wherein the third frequency is higher than the second frequency;
    determining at least a velocity of the third p-wave through the cement composition;
  calculating a first compressibility of the cement composition ($1/K_b$) before its percolation threshold according to a formula:

$$V_s = \left( \frac{K_b + \frac{4}{3}G}{\left[(1-\phi)\rho_s + \left(\phi - 2 + \frac{\alpha}{\phi}\right)\rho_f\right]} \right)^{0.5}$$

wherein $V_s$ is the velocity of the second p-wave through the cement composition, $\phi$ is a porosity of the cement composition, $\alpha$ is a geometric factor and is related to $\phi$ as $\alpha = \frac{1}{2}(1+1/\phi)$, $\rho_s$ is a weighted average density of solid constituents of the cement composition, $\rho_f$ a density of one or more fluid components of the cement composition, and G approaches zero;

calculating a Poisson's ratio of the cement composition ($v$) using the formula:

$$v = \frac{1}{2}\left[\frac{\left(\frac{V_f}{V_{shear}}\right)^2 - 2}{\left(\frac{V_f}{V_{shear}}\right)^2 - 1}\right]$$

wherein $V_f$ is the velocity of the third p-wave and $V_{shear}$ is a velocity of a shear wave through the cement composition;

calculating a Young's modulus of the cement composition (E) using the formula:

$$E = 2V_{shear}^2 \rho(1+v)$$

wherein $\rho$ is a density of the cement composition;

calculating a shear modulus of the cement composition (G) using the formula:

$$G = V_{shear}^2 \rho$$

calculating a second compressibility ($1/K_b$) of the cement composition after its percolation threshold using the formula:

$$K_b = V_f^2 \rho + \frac{4}{3}G$$

determining an attenuation of one or more of the first p-wave and the third p-wave that has been transmitted through the cement composition;

based at least in part on the attenuation of the first p-wave or third p-wave, determining a sonic gel strength of the cement composition;

providing a fixed amount of an inert gas in a cavity in communication with the sample cell;

measuring an initial pressure of the inert gas within the cavity;

measuring a second pressure of the inert gas within the cavity after the cement composition has been allowed to at least partially hydrate; and based at least in part on the initial pressure and the second pressure of the inert gas, calculating a change in volume of the cement composition that has been allowed to at least partially hydrate.

11. The method of claim 10 wherein:
the Poisson's ratio of the cement composition, the Young's modulus of the cement composition, the shear modulus of the cement composition, the first compressibility of the cement composition, the second compressibility of the cement composition, the sonic gel strength of the cement composition, and the change in volume of the cement composition are calculated using an information handling system; and
the information handling system receives one or more signals indicative of or used to determine the velocities of the first p-wave, the second p-wave, and the third p-wave.

12. The method of claim 10 wherein the frequencies of the first p-wave and the third p-wave are from about 600 kHz to about 800 kHz, and the frequency of the second p-wave is from about 50 kHz to about 200 kHz.

13. The method of claim 10 further comprising:
based at least in part on one or more of the Poisson's ratio of the cement composition, the Young's modulus of the cement composition, the shear modulus of the cement composition, the first compressibility of the cement composition, and the second compressibility of the cement composition, selecting a downhole cementing fluid for use in an operation in a subterranean formation, wherein the downhole cementing fluid comprises one or more of the same components as the cement composition; and
introducing the downhole cementing fluid into at least a portion of the subterranean formation.

* * * * *